United States Patent [19]

Henderson et al.

[11] Patent Number: 5,625,038
[45] Date of Patent: Apr. 29, 1997

[54] MONOCLONAL ANTIBODIES SPECIFIC FOR *ERYSIPELOTHRIX RHUSIOPATHIAE*

[76] Inventors: Louise M. Henderson, 2106 Barr Dr., Ames, Iowa 50010-4932; Patricia S. Jenkins, 2608 Northwestern, Ames, Iowa 50010; Katharine F. Scheevel, 606 11th St., Nevada, Iowa 50201

[21] Appl. No.: 281,220

[22] Filed: Jul. 27, 1994

[51] Int. Cl.$^6$ .............................. C12N 5/12; C07K 16/12
[52] U.S. Cl. ..................... 530/388.4; 530/388.1; 530/387.1; 424/150.1
[58] Field of Search ............... 530/388.4, 388.1; 424/150.1, 141.1

[56] References Cited

PUBLICATIONS

Cross, A.S. et al, Infection & Immunity, 61(7):2741–2747, Jul. 1993.
Waldmann, T.A., Science, 252:1657–1662, Jun. 1991.
Osband, M.E. et al, Immunology Today, 11(6):193–195, 1990.
Harris, W.J. et al, TIBTECH, 11:42–44, Feb. 1993.
Zesonis, A et al, Scand. J. Rheumatol, 21(2):60–67, 1992.
Galan, J.E et al, Infect & Immun, 58(9):3116–3121, Sep. 1990.
Chin, J.C et al, Vet. Microbiology, 31:169–180, 1992.

*Primary Examiner*—Susan A. Loring
*Attorney, Agent, or Firm*—Glenna Hendricks; M. Howard Silverstein; Stephen Gates

[57] ABSTRACT

Monoclonal antibodies specific for an immunogen of *Erysipelothrix rhusiopathiae* can protect from lethal effects of infection with *E. rhusiopathiae*. The antibodies also are useful for evaluating the potency of vaccines against the pathogenic effects of that organism.

3 Claims, No Drawings

MONOCLONAL ANTIBODIES SPECIFIC FOR *ERYSIPELOTHRIX RHUSIOPATHIAE*

FIELD OF THE INVENTION

This invention relates to monoclonal antibodies specific for an immunogen of *Erysipelothrix rhusiopathiae*. The preferred MAb can protect from lethal effects of infection with *E. rhusiopathiae*, and also has use for evaluating the potency of vaccines against the pathogenic effects of that organism.

BACKGROUND OF THE INVENTION

*Erysipelothrix rhusiopathiae* is a gram-positive, rod-shaped, nonmotile, nonsporulating, facultatively anaerobic bacterium that is widely distributed in nature and is a commensal of the oropharyngeal and intestinal mucosa of various mammals, fish, and birds. Opportunistic entry of the organism into deeper tissues results in disease in a variety of hosts, including humans. Human infection is frequently associated with occupational exposure to the microorganism and may result in a variety of clinical conditions, including skin lesions and acute or subacute endocarditis. Swine, lamb, and turkey erysipelas cause significant economic losses and can result in exposure of humans to the agent. Clinical signs of disease in swine range from subacute urticarial lesions to chronic arthritis and/or endocarditis to acute septicemia and death.

Because *E. rhusiopathiae* is a facultative intracellular pathogen that survives well within mouse peritoneal macrophages and pig polymorphonuclear neutrophils, protection of swine from disease is thought to rely on eliciting both humoral and cell-mediated immunity. Commercial vaccines have been shown to elicit cross-protective immunity to challenge with serotypes 1 and 2. Although both cross-reactive and serotype-specific antibodies are elicited in swine by exposure to the organism, not all elicited antibodies are protective in nature, and a serological response to whole-cell antigen does not correlate with immunity following challenge-exposure to the agent.

There are a number of USDA-licensed whole-cell bacterins (killed vaccines) and modified-live virus vaccines useful in the control of swine erysipelas. However, it has been suggested that vaccination of swine may lead to an increase in arthritic lesions, possibly as a result of hypersensitization of the animal to subsequent exposure to virulent *E. rhusiopathiae*. Previously reported monoclonal antibodies have been shown to prevent the development of polyarthritis induced by experimental infection with *E. rhusiopathiae* in rats. There was evidence that prevention of disease by the previously reported monoclonal antibody was not due to classical passive immunization, but rather to monoclonal antibody activation of host immune responses. The previously reported monoclonal antibody was not protective when given with or after the challenge-exposure.

Whole-cell and detergent-solubilized surface protein extracts of *E. rhusiopathiae* have been shown to contain a number of immunogens; however, most immunogens have not been examined with respect to the ability to induce a protective response or a hypersensitizing response. Of particular interest is a 64–66 kDa band complex that has been shown to contain 1–4 bands (depending on experimental conditions) that are immunogenic in swine. A gene encoding a protective 64–66 kDa antigen complex was cloned and expressed in *Escherichia coli*. The expressed gene was shown to result in 43 and 64–66 kDa components. The 43 kDa polypeptide is thought to be a processed or degraded form of the 64–66 kDa protein and has been shown to react with antisera that recognizes the 64–66 kDa protein. The recombinant *E. coli* elicited a protective immunologic response in mice. A serological response in swine to a 65 kDa antigen was shown to correlate with a protective immune response. In addition, a 65 kDa antigen, which is highly expressed by *E. rhusiopathiae*, has been shown to share significant homology and antigenic specificity with the *E. coli* DnaK gene product, a 70 kDa heat shock protein (Hsp70). However, it is not known if the 65 kDa protective immunogen is the same protein as that shown to have homology with the Hsp70.

Because the 65 kDa protein has been shown to be an immunodominant detergent-soluble antigen, it has been suggested that if the protective immunogen(s) are different from the sensitizing immunogen(s), a subunit vaccine composed of only protective immunogens, such as the 65 kDa protein, would provide a safer vaccine. Ideally, a subunit vaccine would protect against both the acute and chronic forms of the disease without detrimental hypersensitizing effects such as arthritis. A subunit vaccine might also provide a means for a diagnostic serologic assay for differentiating vaccinates from those animals exposed to field strains of *E. rhusiopathiae*.

Heat shock proteins and other bacterial stress proteins have been associated with protective host immune responses and have been identified as immunodominant B-cell antigens of diverse bacterial pathogens. It has been postulated that these abundant stress proteins may have immunoprophylactic potential for a broad spectrum of pathogens. The DnaK protein is a member of a highly conserved family of proteins found in all living cells that function in the translocation of proteins across cell membranes, most likely by acting as molecular chaperones. These proteins are abundantly produced by bacterial cells during an infective process. For these reasons, it was felt likely that a hybridoma secreting monoclonal antibodies (MAb) to the *E. rhusiopathiae* 64–66 kDa polypeptide would be useful for potency testing of erysipelas bacterins.

DETAILED DESCRIPTION OF THE INVENTION

A hybridoma secreting monoclonal antibody (MAb) specific for a 64–66 kDa polypeptide from *E. rhusiopathiae* has now been developed. The MAb is specific for a primarily proteinascous epitope common to all strains of *E. rhusiopathiae* tested. The ability of the MAb to provide passive protection from challenge-exposure to virulent *E. rhusiopathiae* has been demonstrated in mice and swine. The MAb is administered to susceptible hosts to prevent morbidity in the exposed animals. The antibodies are also useful for antigenic quantitation of bacterins containing *E. rhusiopathiae*, for diagnostic serologic tests for determination of immune status, and for use in purifying antigens for a subunit vaccine.

MATERIALS AND METHODS

Bacterial strains and growth conditions—For development of the MAb, the National Veterinary Service Laboratories (NVSL) *E. rhusiopathiae* reference bacterin, Internal Reference Preparation *E. rhusiopathiae* Bacterin Serial 3,[1] (IRP ERB-3), which contains strains SE-9, CN-3461, CN-3342, and AN-4, was used to vaccinate mice. The following strains of *E. rhusiopathiae* were used to test the MAb: E1-6P, SE-9, CN-3461, CN-3342, and AN-4, all of which are serotype 1 or 2.[2] Strain E1-6P is a pig-virulent challenge strain; all other strains are bacterin strains representing the strains most commonly used for bacterin production. The challenge culture for animal protection studies was the NVSL Internal Reference Preparation *E. rhusiopathiae* Challenge Serial 3 (IRP ERC-3), strain E1-6P.[a] For growth, cultures of *E. rhusiopathiae* were used to inoculate Columbia agar plates with 10% bovine blood, blood agar plates, or supplemented horse meat and liver infusion media. Inoculated Columbia agar plates were incubated in a 10% $CO_2$ atmosphere at 37° C. for 18–48 hours for growth. Other inoculated media were incubated at 37° C. for 18–48 hours for growth.

[1] Available from the National Veterinary Services Laboratories, PO Box 844, Ames, Iowa 50010.
[2] Originally obtained from R. L. Wood, National Animal Disease Center, Agricultural Research Service, United States Department of Agriculture, Ames, Iowa 50010.

Supplemented horse meat and liver infusion broth—Meat infusion was made by dispersing 454 gm ground horse meat and 18 gm ground horse liver in 1 liter of distilled water and simmering for 1 hour just below boiling. The mixture was boiled for 5 minutes and allowed to cool and settle for 2 hours. The broth was filtered through No. 2 Whatman filter paper. To 1 liter of filtered broth, 20 g peptone, 10 ml ox bile, 5 g gelatin, 11 g dibasic anhydrous sodium phosphate, and 1 g monobasic potassium phosphate were added. The pH was adjusted to 8.0 with 5N sodium hydroxide and filtered through a Model 7B Hormann filter using filter grades D5 and D9. Just prior to inoculation, medium was autoclaved at 115° C. at 15 lbs pressure for 75 minutes, the final pH was adjusted to 7.6 to 7.8, and 100 ml of sterile normal horse serum and 5 ml of sterile 50% dextrose solution were aseptically added to the medium.

Whole-cell and supernatant preparation—Strains of *E. rhusiopathiae* were grown as described. Ten ml of culture was centrifuged at 6000×g for 10 minutes, and the supernatant was separated from the whole-cell pellet. Equal amounts of supernatant and 2X sample buffer or whole-cell pellet and 1X sample buffer were mixed and used for Western blot analyses.

Challenge culture preparation—The challenge-exposure inocula was prepared as follows: 10 ml of supplemented horse meat and liver infusion broth was inoculated with the *E. rhusiopathiae* challenge culture, IRP ERC-3, and incubated overnight at 37° C. A 100 ml amount of supplemented horse meat and liver infusion broth was inoculated with 10 ml of the overnight culture and incubated for 3–4 hours. The culture was adjusted to 40% light transmission at 600 nm (% $T_{600}$) with sterile medium. Serial tenfold dilutions were made in sterile medium from $10^{-1}$ to $10^{-8}$.

Cell suspensions—Ten ml of supplemented horse meat and liver infusion media was inoculated with individual strains of *E. rhusiopathiae* and incubated at 37° C. for 18 hours. The cultures were centrifuged at 6000×g for 15 minutes at 4° C. The supernatant was discarded, and the cells were resuspended in 10 ml phosphate buffered saline (PBS), pH 7.2. The cells were centrifuged at 6000×g for 15 minutes at 4° C. and the supernatant was discarded. The cells were resuspended in 10 ml PBS, and the suspension was held at 4° C. overnight.

Extracted antigen—Antigen extractions were made by centrifuging 2 ml of cell suspension at 10,000×g for 3 minutes. The supernatant was discarded and the cells resuspended in 500 µl of a 1 mM Tris solution (pH 7.5) containing 10 mM sodium dodecyl sulfate (SDS). Suspensions were incubated at 37° C. for 30 minutes in a water bath and centrifuged at 10,000×g for 3 minutes. The pellet was discarded and the supernatant was used for Western blot analyses.

Sonicated antigen—Sonicated antigen was prepared by sonicating 3.0 ml cell suspensions for 1 minute at 50% duty cycle, 40 watts, 20 khz, on ice, using an ultrasonic processor with a microtip. Cells were sonicated three times, with a 1 minute incubation on ice between each sonication. The sonicated antigens were used for the screening enzyme-linked immunosorbent assay (ELISA).

SDS/PAGE and Western immunoblot analyses—SDS polyacrylamide gel electrophoresis (SDS/PAGE) and Western blot analyses were performed according to the method of Laemmli. (Laemmli UK. Cleavage of structural proteins during the assembly of the head of the bacteriophage T4. *Nature* 1970;227:680. Smith JA. In: *Current Protocols in Molecular Biology*. F. Ausubel et al., eds. John Wiley and Sons, New York, 1987.) Extracted antigen, whole-cell antigen, or supernatant was diluted 1:1 in 2X sample buffer (0.12M Tris-HCl, pH 6.8, 2.5% SDS, 0.005% bromophenol blue, 20% glycerol, 5% β-mercaptoethanol), boiled for 5 minutes in a 100° C. water bath, and subjected to electrophoresis through a 2-D 10% acrylamide gel in running buffer (25 mM Tris, 193 mM glycine, 0.1% SDS, pH 8.0) at 30 mA for 2–4 hours. Molecular weight standards were placed in the first well of the gel and used to determine the apparent molecular weight (molecular mass) of the antigens. The separated proteins were electroblotted to nitrocellulose membranes at 250 mA for 2 hours in transfer buffer (12 mM Tris, 96 mM glycine, pHS.3, with 20% methanol). The membranes were blocked at room temperature for 15 minutes in 1% bovine serum albumin fraction V (BSA) in PBS. Polyclonal antisera diluted 1:200, undiluted individual hybridoma cell culture supernatant, or undiluted ascites were adsorbed to the nitrocellulose for 2 hours at 37° C. Membranes were washed three times for 5 minutes each in 0.15M PBS containing 0.5% Tween 20 (PBST) and reblocked in BSA. Horseradish peroxidase (HRP)-labelled anti-mouse or anti-swine IgG[3] diluted 1:1000 in BSA was adsorbed to the membrane for 2 hours at 37° C. The membranes were washed three times for 5 minutes each in PBST Freshly prepared 3,3',5,5'-tetramethylbenzidine substrate (TMB) with TMB membrane enhancer[c] (prepared according to manufacturer's instructions) was used as the color substrate. After the color was allowed to develop for up to 30 minutes, membranes were washed 5 times in PBS and air dried.

[3] Kirkegaard and Perry Laboratories, Inc., 2 Cessna Court, Gaithersburg, Md. 20879.

Screening ELISA—A crude ELISA suitable for quantitation of antibodies to whole-cell preparations of *E. rhusiopathiae* was developed for screening hybridoma cell culture supernatants and mouse sera. To determine the immune status of mice prior to harvesting the spleen for hybridoma production and to detect those hybridomas secreting antibodies directed against *E. rhusiopathiae*, 20 µl of sonicated antigen from strain E1-6P was diluted in 10 ml antigen coating buffer (0.5M carbonate buffer, pH 9.6). A 96-well microtitration plate was coated with 100 µl diluted antigen/well and incubated at 37° C. for 1 hour. The plate was stored overnight at 4° C. and washed the following morning. All washes consisted of aspiration followed by three washes with 350 µl of 0.15M phosphate-buffered saline with 0.05% Tween 20 using a Dynatech II automatic microtitration plate washer. A 100 µl amount of serially diluted mouse serum or of serially diluted hybridoma cell culture supernatant was placed in each well and the plate was incubated at 37° C. for 2 hours. The plate was washed, and a 100 µl amount of HRP-labelled anti-mouse IgG diluted 1:1000 in PBS was placed in each well. The plate was incubated at 37° C. for 2 hours and washed. A 100 µl amount of freshly-prepared 2,2'-azino-di-3-ethylbenzthiazoline sulfonate (ABTS) substrate[c] was added to each well, the color was allowed to develop, and the $O.D._{405}$ was determined using a microtiter ELISA reader.

Polyclonal antisera production—Mice and swine were immunized with the NVSL reference bacterin, Internal Reference Preparation *E. rhusiopathiae* Bacterin Serial 3 (IRP ERB-3), an aluminum hydroxide-adjuvanted reference bacterin produced by the NVSL, by intraperitoneal (IP) injection of 0.2 ml into mice and 2.0 ml into swine. Two weeks after vaccination, vaccinated animals were challenged with a virulent culture of IRP ERC-3, as previously described.[1] Blood was collected from survivors that demonstrated no clinical signs, and sera was frozen at −20° C. or lower.

Production of monoclonal antibodies—The MAbs were produced by the method of Van Deusen and Whetstone.[2] Briefly, 4 BALB/c mice were injected IP with 0.2 ml of IRP ERB-3 on Days 0 and 21. On Day 42, mice were bled and the sera were assayed using the screening ELISA. A mouse with a high ELISA titer was selected and injected IP with 0.2 ml of IRP ERB-3. On Day 4 after the third injection, the spleen was harvested and spleen cells were fused with $Sp_2/0$ cells in the presence of polyethylene glycol. Over 600 hybridomas were assayed for production of anti-*E. rhusiopathiae* antibodies using the screening ELISA. Of these, over 100 secreting hybridomas were selected for Western blot analyses. A total of fifteen cloned hybridomas that reacted with either the 66 kDa immunogen of interest or with other immunogens common to all strains of the organism by Western blot were selected. Selected clones were then subcloned, and the resulting supernatants from the twice-cloned hybridomas were again tested by ELISA and Western blot. Further selection was based on the results of the ELISA and the Western blot analyses.

Production of ascites fluid—BALB/c mice were primed by IP injection of 0.5 ml 2,6,10,14-tetramethylpentadecane (pristane) at least 3 weeks prior to ascites production. Cells from the subclones selected by results of Western blot analyses were washed twice in PBS and resuspended to a concentration of $2 \times 10^6$ cells/ml. A 0.5 ml amount was injected IP into each mouse. Ascites fluid was collected by IP puncture three times a week following tumor development until ascites fluid production ceased, up to a maximum of four collections. The ascites fluid was centrifuged at 6000×g for 15 minutes to remove particulate material and the supernatant was frozen at −20° C. immediately following harvesting. Following collection, the ascites fluid was pooled to produce a pool of ascites fluid with a constant titer and stored at −20° C.

Negative control ascites fluid was prepared in the same manner using a hybridoma recognizing *Leptospira interogans* serotype *grippotyphosa* (C73A9AF). Western blot analyses demonstrated no reactivity to whole-cell *E. rhusiopathiae*.

Conjugation of MAb to enzyme—The ascites fluid was conjugated with HRP according to established procedures.[3,4] Briefly, the ascites fluid was fractionated twice with saturated ammonium sulfate, dialyzed until free of sulfate ions, reacted with freshly prepared peroxidase-aldehyde solution, and purified.

Animals—BALB/c mice were used for MAb and ascites fluid production. Harlan Sprague Dawley CF-1 white males (18–25 g each) were used in the mouse challenge-exposure studies. Crossbred pigs (6 weeks old) with no known previous exposure to *E. rhusiopathiae* were used in the swine challenge-exposure study.

In vivo studies:

Challenge-exposure of mice and swine—Challenge-exposure and passive protection challenge-exposure followed the Code of Federal Regulations Title 9 recommendations for a mouse potency assay for erysipelas bacterins (9CFR Section 113.119) or swine challenge-exposure recommendations for establishing host efficacy (9CFR Section 113.67).

For preliminary challenge-exposure studies, equal amounts of hybridoma cell culture supernatant were mixed with each of the challenge culture dilutions ($10^{-1}$ to $10^{-8}$). The challenge culture-hybridoma supernatant mixtures were incubated at 37° C. for 1 hour. Mice were injected IP with either 0.2 ml challenge culture, 0.4 ml mixture of challenge culture-hybridoma supernatant, or 0.4 ml mixture of challenge culture-ascites fluid. Mice were observed for 7 days and deaths were recorded.

For the preliminary swine challenge-exposure studies, the challenge culture was prepared and a $10^{-5}$ dilution of the challenge culture was diluted 1:1 in the selected ascites fluid and incubated for 1 hour at 37° C. Swine were injected IM with 2.0 ml culture mixed with 2.0 ml ascites fluid. Control swine were injected with 2.0 ml culture. Rectal temperatures were monitored and clinical signs were observed for 7 days. Swine were considered susceptible to challenge-exposure if they met requirements stated in the 9CFR; that is, if rectal temperatures were above 40.9° C. for 2 or more consecutive days and/or clinical signs of erysipelas were manifested.

Passive protection of mice and swine—Passive protection studies of mice and swine were performed by injection of mice with 0.5 ml ascites fluid by IP injection on Day 1 and challenge-exposure to 0.2 ml challenge culture (diluted $10^{-4}$ to $10^{-7}$) by SC injection on Day 2. Mice were observed for 7 days and deaths were recorded.

For swine passive protection studies, swine were injected with 5.0 ml ascites fluid by IV injection on Day 1 and challenge-exposed by IM injection of 2.0 ml of a $10^{-5}$ dilution of challenge culture on Day 2. Test ascites fluid was ERHU1-B60-91. Control ascites fluid was C73A9AF. Rectal temperatures were monitored and clinical signs were observed for 7 days.

RESULTS

Immunogens common to tested strains of *E. rhusiopathiae*—Whole-cell and supernatant (spent culture broth) preparations of five strains of *E. rhusiopathiae* were prepared and a Western blot was preformed. The blots were reacted with either polyclonal mouse sera or polyclonal swine sera. Results demonstrated a number of immunogens recognized by serum antibody from both mice and swine, including immunodominant bands of 65–70 kDa and 46 kDa.

Challenge-exposure studies in mice—Cell culture supernatants from 7 hybridomas that reacted with the 65 kDa polypeptide and 6 hybridomas that reacted with other *E. rhusiopathiae* immunogens were selected for challenge-exposure studies in mice using a single $10^{-8}$ dilution of challenge culture. Mice were challenge-exposed by IP injection of 0.4 ml mixture consisting of 0.2 ml $10^{-8}$ dilution of challenge culture and 0.2 ml hybridoma cell culture supernatant. Mice were observed for 7 days, and deaths were recorded (Table 1). Protection was defined as a lower death loss from challenge-exposure of the group exposed to the test fluids. Only 2 of the first 13 hybridoma cell culture supernatants, ERHU1-B60-91 and ERHU1-B58-BB2-9, demonstrated the ability to lower the death loss in the first challenge-exposure study. The 2 protective MAb, ERHU1-

B60-91 and ERHU1-B58-BB2-9, both of which recognized a 65 kDa polypeptide immunogen, were selected for ascites titration challenge-exposure studies in mice. Ascites fluids were produced and mice were challenge-exposed using $10^{-1}$ to $10^{-9}$ dilutions of challenge culture mixed with 0.2 ml of ascites fluid. Mice were observed for 7 days following challenge-exposure, and deaths were recorded (Table 2). Both ascites fluids lowered the death loss in challenge-exposed mice. Although the exact dose required to kill 50% of the challenged mice (lethal dose$_{50}$, LD$_{50}$) could not be calculated because higher dilutions of challenge culture were not tested, ascites fluid from hybridoma ERHU1-B58-BB2-91 increased the LD$_{50}$ by an estimated factor of 10. Hybridoma ERHU1-B60-91 increased the LD$_{50}$ by at least $10^5$. ERHU1-B60-91 was chosen for further study because of the higher level of protection from death loss it provided.

TABLE 1

Ability of 13 cell culture supernatants to provide protection from challenge-exposure in mice. Control mice were challenge-exposed by IP injection to virulent culture. Test mice were challenge-exposed by IP injection to a 1:1 mixture of virulent culture and undiluted hybridoma cell culture supernatants. Mice were observed for death loss for 7 days from challenge-exposure.

| Hybridoma | Band(s) Recognized | Survivors/Challenged |
|---|---|---|
| ERHU1-AH-12 | 30 | 0/30 |
| ERHU1-BE-12 | 30, 43, 66 | 0/30 |
| ERHU1-AG-9 | 30, 43, 66 | 0/30 |
| Control | | 0/10 |
| ERHU1-A-52 | 28 | 0/10 |
| ERHU1-B-58 | 43, 66 | 0/10 |
| Control | | 0/10 |
| ERHU1-C18-5 | 43, 66 | 0/6 |
| ERHU1-B41-A8 | 21 | 0/6 |
| ERHU1-B41-C6 | 46 | 0/6 |
| ERHU1-A59-AA7 | 43, 66 | 0/6 |
| ERHU1-A52-AG9 | 30 | 0/6 |
| ERHU1-B41-B5 | 43 | 0/6 |
| ERHU1-B58-BB2-9 | 43, 66 | 5/6 |
| ERHU1-B60-91 | 43, 66 | 5/6 |
| Control | | 0/6 |

TABLE 2

Challenge-exposure studies of ERHU1-B60-91 and ERHU1-B58-BB2-9 in mice. Control mice were challenge-exposed to virulent culture. ERHU1-B58-BB2-9 was challenge-exposed to virulent culture mixed with ERHU1-B58-BB2-9 ascites fluid. ERHU1-B60-91 was challenged-exposed to virulent culture mixed with ERHU1-B60-91 ascites fluid. Results are expressed as number of survivors/10 mice challenged.

| Challenge dilution | Controls | ERHU1-B58-BB2-9 | ERHU1-B60-91 |
|---|---|---|---|
| $10^{1-}$ | ND | 0 | 6 |
| $10^{-2}$ | ND | 0 | 5 |
| $10^{-3}$ | ND | 0 | 2 |
| $10^{-4}$ | ND | 0 | 6 |
| $10^{-5}$ | 0 | 0 | 10 |
| $10^{-6}$ | 0 | 1 | 9 |
| $10^{-7}$ | 0 | 1 | 10 |
| $10^{-8}$ | 1 | 5 | 10 |
| $10^{-9}$ | 8 | ND | ND |

ND: not determined

Challenge-exposure studies in swine—Group 1 (Pigs 51 and 52) were injected IM with 2.0 ml of the selected ascites fluid, ERHU1-B60-91, and observed for 48 hours for adverse reactions. No adverse reactions were observed. Group 2 (Pig 53–55) and Group 3 (Pigs 56–60) did not receive ascites fluid prior to challenge-exposure. Pigs were challenge-exposed using a $10^{-5}$ dilution of challenge culture. Group 1 (Pigs 51 and 52) and Group 2 (Pigs 53–55) were injected IM with 2.0 ml of a $10^{-5}$ dilution of culture mixed with 2.0 ml ascites fluid. Group 3 (Pigs 56–60) were injected with 2.0 ml of a $10^{-5}$ dilution of culture. Colony counts indicated a challenge of $3\times10^{10}$ organisms/ml ($6\times10^{10}$ organisms/dose). Clinical signs and death in Groups 1 and 2 were compared to that of Group 3.

The ability of ERHU1-B60-91 to reduce clinical signs in swine from challenge-exposure when mixed with the challenge culture was demonstrated by lower rectal temperatures, fewer clinical signs manifested, and fewer deaths observed in Groups 1 and 2 compared to Group 3 (Table 3). The challenge resulted in the death of three of the five control pigs in Group 3. Rectal temperatures above 40.9° C. for 2 or more consecutive days and manifestations of characteristic clinical signs were observed in all control pigs. No pigs died in Groups 1 and 2, the groups exposed to challenge culture mixed with ERHU1-B60-91. One of the test pigs was protected from all clinical signs and was considered immune to challenge-exposure. In addition, clinical signs and rectal temperatures in all test pigs were significantly decreased as compared to the control pigs. Clinical signs were lowest in Group 1, which is likely due to the increased amount of ascites fluid injected into pigs in Group 1.

TABLE 3

Challenge-exposure studies of ERHU1-B60-91 ascites fluid against *E. rhusiopathiae*. Group 1 (Pigs 51 and 52) received 2 ml ERHU1-B60-91 ascites fluid 48 hours prior to challenge-exposure. Group 1 and Group 2 (Pigs 53–55) were challenge-exposed to virulent culture mixed with ascites fluid. Group 3 (Pigs 56–60) was challenged with virulent culture.

| No. | Gr | 2 dpi | 3 dpi | 4 dpi | 5 dpi | 6 dpi | 7 dpi |
|---|---|---|---|---|---|---|---|
| 51 | 1 | N | T, S | T, S | N | N | N |
| 52 | 1 | N | N | N | N | N | N |
| 53 | 2 | N | N | N | S | S, L | S, L, E |
| 54 | 2 | N | N | N | N | T, S | T, S, E |
| 55 | 2 | N | T, S | S, W | T, S, L, E | T, L, E, W | T, E, S |
| 56 | 3 | T | T | T, S, E | T, S, E, G | E, S, G | E |
| 57 | 3 | S | T, E, S | Dead | | | |
| 58 | 3 | T, S | Dead | | | | |
| 59 | 3 | T, S, G, W | Dead | | | | |
| 60 | 3 | N | T | T, S, W | T, E, S | T, E | E |

N: no clinical signs observed
T: rectal temperature elevated above 105.6° F.
S: sluggish
L: lame
E: erythema
W: weak
G: gaunt Passive protection studies in mice and swine—On Day 1, 40 mice were injected IP with 0.5 ml of ERHU1-B60-91 ascites fluid, 40 mice were injected IP with 0.5 ml of C73A9AF, a negative control ascites fluid with no reactivity to *E. rhusiopathiae*, and 40 control mice received no ascites fluid. On Day 2, mice were challenge-exposed to 0.2 ml of challenge culture diluted $10^{-4}$ to $10^{-7}$ (10 mice/group/dilution). Mice were observed for 7 days and deaths recorded (Table 4). Results demonstrate passive protection of mice from death due to challenge-exposure to IRP ERC-3.

For swine passive protection studies, Group 4 (Pigs 14, 90, 94, 96, and 99) were injected with 5.0 ml C73A9AF ascites fluid and Group 5 (Pigs 13, 15, 95, 98, and 100) were injected with 5.0 ml ERHU1-B60-91 ascites fluid by IV injection on Day 1. On Day 2, swine were challenge-exposed by IM injection to 2.0 ml of a $10^{-5}$ dilution of challenge culture. Rectal temperatures were monitored and swine were observed for 7 days for clinical signs. Results of the swine passive protection studies demonstrate passive protection from clinical signs of disease by ERHU1-B60-91 (Table 5).

TABLE 4

Passive protection studies of ERHU1-B60-91 in mice. Mice were injected with 0.5 ml PBS, 0.5 ML ERHU1-B60-91 ascites fluid, or 0.5 ml C73A94AF (negative control) ascites fluid on Day 1 and challenge-exposed by SC injection of 0.2 ml diluted challenge culture on Day 2. Deaths were observed for 10 days. Results are expressed as number of survivors/10 mice challenged.

| Challenge dilution | Controls | C73A9AF | ERHU1-B60-91 |
|---|---|---|---|
| $10^{-4}$ | 0 | 0 | 10 |
| $10^{-5}$ | 0 | 0 | 9 |
| $10^{-6}$ | 0 | 0 | 10 |
| $10^{-7}$ | 0 | 0 | 10 |

TABLE 5

Passive protection studies of ERHU1-B60-91 ascites fluid against *E. rhusiopathiae*. Group 4 (Pigs 14, 90, 94, 96, and 99) received 5.0 ml C73A9AF (negative control) ascites fluid on Day 1. Group 5 (Pigs 13, 15, 95, 98, and 100) received 5.0 ml ERHU1-B60-91 ascites fluid on Day 1. All pigs were challenge-exposed by IM injection of 2.0 ml $10^{-5}$ dilution of challenge culture on Day 2. Clinical signs were assessed for 7 day.

| No. | Day 3 | Day 4 | Day 5 | Day 6 | Day 7 | Day 8 | Day 9 |
|---|---|---|---|---|---|---|---|
| 14 | N | T, S | T, S | T, S, E | Dead | | |
| 90 | N | T, S | T, S | T, W, E | T, W, E | W, E | Dead |
| 94 | T | T, S | T, S | T, S, L | L | W, L | Dead |
| 96 | T | T, S, W | T, E, W | T, E, W | Dead | | |
| 99 | T | N | T | N | N | N | N |
| 13 | N | N | N | N | N | N | N |
| 15 | N | N | N | N | N | N | N |
| 95 | N | N | N | N | N | N | N |
| 98 | N | N | N | N | N | N | N |
| 100 | N | N | N | N | N | N | N |

N: no clinical signs observed
T: rectal temperature elevated above 105.6° F.
S: sluggish
L: lame
E: erythema
W: weak
G: gaunt ERHU1-B60-91MAb characterization—Western blot analyses of ERHU1-B60-91 demonstrated the ability of the MAb to recognize the 65 kDa immunogen in 5 strains of *E. rhusiopathiae*. Results of the Western blot analyses using the HRP-labelled MAb were similar. The subisotype of the ERHU1-B60-91 ascites tumor fluid was determined using a commercial isotype kit and following the manufacturer's recommendations (Hyclone, Logan, Utah). Results indicated an $IgG_1$ isotype. To determine the nature of the epitope recognized by the Mab, extractions of five strains of *E. rhusiopathiae* were treated with 0.2% proteinase K at 37° C. for 2 hours followed by 55° C. for 2 hours. Treated and untreated samples of each strain were subjected to SDS/PAGE and Western blot analyses using the ERHU1-B60-91MAb as the primary antibody. The test was repeated using HRP-conjugated ERHU1-B60-91. The extraction procedure resulted in the ability to detect a large number of bands by the MAb due to the presence of breakdown products of the polypeptide. Proteinase K destroyed the epitope(s) recognized by ERHU1-B60-91. These results demonstrate a predominant protein component of the epitope recognized by the MAb.

Assay using a direct enzyme-linked immunosorbent assay (ELISA):

Following is an in vitro assay method using a direct enzyme-linked immunosorbent assay (ELISA) system to measure the relative potency of bacterins containing *Erysipelothrix rhusiopathiae.*

POTENCY TESTING

In vitro assay method using a direct enzyme-linked immunosorbent assay (ELISA) system to measure the relative potency of bacterins containing *Erysipelothrix rhusiopathiae*.

MATERIALS

1. Potassium phosphate elution buffer

| | |
|---|---|
| $KH_2PO_4$ | 8.2 g |
| Deionized water | q.s. to 100 ml |
| pH to 6.5 | |

2. Bacterins containing *E. rhusiopathiae* antigen
   a. Reference bacterin
   b. Test serial ( s )
3. Phosphate buffered saline, pH 7.2 (PBS)

| | |
|---|---|
| NaCl | 8.0 g |
| KCl | 0.2 g |
| $Na_2HPO_4$ | 1.15 g |
| $KH_2PO_4$ | 0.2 g |
| Deionized water | q.s. to 1000 ml |
| Adjust pH to 7.2 with 0.1M NaOH or 0.1M HCl | |

4. 0.5% sodium desoxycholate

| | |
|---|---|
| PBS, pH 7.2 | 100 ml |
| Sodium desoxycholate | 0.50 g |
| (Difco Cat. No. 02248-13, Sigma D-6750, or equivalent) | |
| Store at 4° C. up to 30 days; warm to 22° C. prior to use | |

5. Antigen coating buffer (0.5M carbonate buffer, pH 9.6)

| | |
|---|---|
| $Na_2CO_3$ | 1.59 g |
| $NaHCO_3$ | 2.93 g |
| Deionized water | q.s. to 1 liter |
| Store at 4° C. for up to 1 week | |

6. Sodium citrate ($Na_3C_6H_5O_7$'2 $H_2O$; F. W. 294.10)
7. Wash solution (phosphate buffered saline, pH 7.2, 0.05% Tween 20)

| | |
|---|---|
| Tween 20 | 0.5 ml |
| PBS, pH 7.2 | 1000 ml |

8. Blocker solution (Use 1 or 2)

| 1. 5% nonfat dry milk (NFDM) | |
|---|---|
| Nonfat dry milk | 5.0 g |
| PBS, pH 7.2 | 100 ml |
| Make fresh daily | |
| 2. 1% Polyvinyl alcohol (PVA) | |
| PVA (80% hydrolyzed 13,000 MW) | 1.0 g |
| PBS, pH 7.2 | 100 ml |
| Make fresh daily. Store at room temperature (20–25° C.). | |

9. Antibodies a. *E. rhusiopathiae* monoclonal antibody (MAb) ERHU1-B60-91 in the form of ascites fluid obtained from the National Veterinary Services Laboratories (NVSL). The MAb is stored at −20° C.

b. Conjugate is goat anti-mouse IgG horseradish-peroxidase (HRP) labelled antibody (Kirkegaard & Perry Laboratories, Inc., 2 Cessna Court, Gaithersburg, Md. 20879, #04-18-06 or equivalent). Alternately, donkey anti-mouse IgG HRP labelled antibody (Jackson Immunoresearch Laboratories, Inc., PO Box 9, Westgrove, Pa. 19390, #715-0360151 or equivalent) may be used.

10. Substrate (Use 1 or 2)

1. 3,3',5,5'-tetramethylbenzidine (TMB) (Kirkegaard & Perry Laboratories, Inc., 2 Cessna Court, Gaithersburg, Md. 20879, #50-76-00 or equivalent).

2. 2,2'-azino-di-3-ethylbenzthiazoline sulfonate (ABTS) (Kirkegaard & Perry Laboratories, Inc., 2 Cessna Court, Gaithersburg, Md. 20879, #50-62-00 or equivalent).

11. Stop solution for TMB: 2.5M $H_2SO_4$

PROCEDURES

1. Preparation of the bacterin(s)

The reference bacterin and test serial bacterin(s) are treated identically. Bacterin containers are shaken by hand or vortexed to thoroughly mix the contents. Some products may be tested prior to elution. Other products may require elution. Products are eluted as necessary using one of the following elution methods:

a. Potassium-phosphate elution

A 5.0 ml aliquot of bacterin is immersed in an ice water bath and sonicated for 1 minute at a duty cycle of 40 at 20 mhz with a microtip using a high intensity 50-watt ultrasonic processor. The sonicated bacterins are diluted in an equal volume of potassium phosphate elution buffer, and the mixtures are incubated at 37° C. overnight (12–18 hours) on a rotary shaker at 80–90 rpm.

b. Freezing-centrifugation elution

For those samples that are not satisfactorily eluted using the potassium-phosphate elution method, at least 5.0 ml of bacterin is frozen at −70° C. for at least 24 hours. Bacterins are thawed at 37° C. and 5.0 ml bacterin is combined with 5.0 ml sodium desoxycholate. A 1 g amount of sodium citrate is added. The mixture is vortexed briefly to dissolve sodium citrate and incubated at room temperature (22° C.±5°) on a rotary shaker at 80–90 rpm for 30 minutes. The mixture is vortexed briefly and incubation is continued an additional 30 minutes. The mixture is centrifuged at 500×g for 10 minutes at 4° C. The supernatant is discarded, and the pellet is resuspended in 5.0 ml potassium phosphate elution buffer. The mixture is immersed in an ice water bath and sonicated for 1 minute at a duty cycle of 40 at 20 mhz with a microtip using a high intensity 50-watt ultrasonic processor. The mixture is incubated overnight (12–18 hours) at 37° C. on a rotary shaker at 80–90 rpm.

ELISA procedure a. Untreated or eluted bacterins are sonicated for 1 minute at a duty cycle of 40 at 20 mhz with a microtip using a high intensity 50-watt ultrasonic processor.

b. A 100 μl amount of antigen coating buffer is placed in each well of an ELISA grade 96-well flat-bottom microtitration plate (Immunlon-2, Dynatech Laboratories, Inc., 14340 Sullyfield Circle, Chantilly, Va. 22021, or equivalent). A 100-μl amount of the eluted bacterin is placed in column 1. At least two replications of the reference bacterin and of each test serial are tested on the same plate. The last well of each column containing the reference bacterin contains only antigen coating buffer instead of bacterin and serves as a blank. Serial twofold dilutions are made by transferring 100 μl from well to well in columns 1 through 12, except in the reference bacterin columns, which are diluted columns 1 through 11.

c. The plate is incubated at 37° C. for 1 hour±15 minutes.

d. An automatic plate washer or equivalent is used to aspirate all wells of the plate. The plate is washed three times with 300 μl wash solution/well.

e. A 300-μl amount of blocker solution is added to each well. The plate is incubated at 37° C. for 1 hour±15 minutes.

f. An automatic plate washer is used to aspirate all wells of the plate. The plate is washed three times with 300 μl wash solution/well.

g. The MAb is diluted in blocker solution to the current use dilution according to the insert instructions. A 100-μl amount of diluted MAb is added to each well. The plate is incubated at 37° C. for 1 hour±15 minutes.

h. An automatic plate washer is used to aspirate all wells of the plate. The plate is washed three times with 300 μl wash solution/well.

i. A 100-μl amount of conjugate diluted to the appropriate dilution (approximately 1:1000) in blocker solution is added to each well. The plate is incubated at 37° C. for 1 hour±15 minutes.

j. An automatic plate washer is used to aspirate all wells of the plate. The plate is washed three times with 300 μl wash solution/well.

k. Substrate is prepared just prior to use. A 100-μl amount of substrate is added to each well. The plate is incubated at room temperature (22°–25° C.) until color is developed.

l. If TMB is used as the substrate, 100-μl of stop solution is added to each well after 5–15 minutes incubation. No stop solution is used with ABTS.

m. The plates are briefly shaken immediately prior to reading, and plates are read at a dual absorbance of 450/650 nm, 405/650 nm, 450/630, or 450/620 on a microplate reader.

n. The mean optical density (O.D.) for all blank wells is determined, and that value is subtracted from all sample O.D. values prior to data analysis.

DATA PROCESSING AND INTERPRETATION

1. Relative potency calculation method: The current version of the National Veterinary Services Laboratories Relative Potency Calculation Program SAM 318 is used to calculate the relative potency of the test serial as compared to that of the reference bacterin. The reference and test serial data are entered, and the program is executed as outlined in SAM 318. The relative potency (RP) value reported for the test serial will be the average of the highest RP values included in the top scores from each replicate.

2. Requirements for a valid assay: An assay must meet the validity requirements of SAM318 (current version) to be considered valid.

a. Lines determined by first-order linear regression must have a correlation coefficient $(r) \geq 0.95$.

b. The reference and test serial lines must show parallelism (slope ratio $\geq 0.80$).

Assays that are not valid may be repeated up to a maximum of three times. If a valid assay cannot be achieved with three independent assays, the serial will be reported as unsatisfactory.

3. Requirements for a satisfactory serial: To be considered satisfactory, a test serial must have an RP value of $\geq 1.0$.

Because MAb ERHU1-B60-91 has been shown to confer protective immunity to challenge with a virulent culture of *E. rhusiopathiae*, it can be used to prevent and treat morbidity in susceptible vertebrates who have been exposed to *E. rhusiopathiae*, whether or not symptoms have developed. The preferred routes of administration are subcutaneous or intravenous injection.

Use of ERHU1-B60-91 in an in vitro assay for the potency testing of *E. rhusiopathiae* bacterins could be used to quantitate a single dominant immunogen that is produced by all strains of the agent. Because production of bacterins is tightly controlled, quantitation of a single essential immunogen may be suitable for potency (antigenic content) testing of bacterins if compared to a reference bacterin produced under the same conditions. Therefore, ERHU1-B60-91 is suitable for the use in in vitro potency assay for erysipelas bacterins.

The MAb can be used for cloning and purification of the 65 kDa immunogen. The protein could then be used to capture immunoglobulin for a serologic diagnostic test or used to produce a subunit vaccine.

The hybridoma cell line producing ERHU1-B60-91 was deposited on May 25, 1994 in the American Type Culture Collection, 12301 Parklawn Drive, Rockville, Md. 20852 and has been awarded the ATCC designation HB 11636.

We claim:

1. A monoclonal antibody which specifically binds *Erysipelothrix rhusiopathiae*, which confers protection against infection by a virulent culture of *Erysipelothrix rhusiopathiae*, wherein said antibody has the protective properties of ERHU1-B60-91, which has been deposited in the American Type Culture Collection and has been assigned the designation HB 11636.

2. A composition of matter comprising ascites fluid containing monclonal antibody ERHU1-B60-91, deposited as HB 11636.

3. A composition of matter comprising the monoclonal antibody of claim 1 in a pharmaceutically acceptable carrier.

* * * * *